United States Patent
Kim et al.

(10) Patent No.: US 9,700,286 B2
(45) Date of Patent: Jul. 11, 2017

(54) FLUID SAMPLE COLLECTION AND TESTING DEVICE

(75) Inventors: James S. Kim, Toronto (CA); Chris R. Parkinson, Hamilton (CA); George Arthur Hossack, Calgary (CA)

(73) Assignee: KPH Diagnostics Inc., Toronto, Ontario (CA)

( * ) Notice: Subject to any disclaimer, the term of this patent is extended or adjusted under 35 U.S.C. 154(b) by 689 days.

(21) Appl. No.: 13/455,550

(22) Filed: Apr. 25, 2012

(65) Prior Publication Data

US 2013/0289443 A1    Oct. 31, 2013

(51) Int. Cl.
| | |
|---|---|
| *A61B 5/00* | (2006.01) |
| *A61B 10/00* | (2006.01) |
| *G01N 33/52* | (2006.01) |
| *A61B 5/15* | (2006.01) |
| *A61B 5/157* | (2006.01) |
| *A61B 5/145* | (2006.01) |

(52) U.S. Cl.
CPC .......... *A61B 10/0045* (2013.01); *A61B 5/157* (2013.01); *A61B 5/150045* (2013.01); *A61B 5/150343* (2013.01); *A61B 5/150358* (2013.01); *G01N 33/528* (2013.01); *A61B 5/14507* (2013.01); *A61B 5/14539* (2013.01); *A61B 5/14546* (2013.01); *A61B 5/4337* (2013.01); *A61B 2010/0074* (2013.01)

(58) Field of Classification Search
CPC .......... A61B 5/1411; A61B 2010/0074; A61B 10/0045; A61B 5/14507; A61B 5/14539; G01N 33/528
USPC ....................................................... 600/584
See application file for complete search history.

(56) References Cited

U.S. PATENT DOCUMENTS

| | | |
|---|---|---|
| 3,897,214 A | 7/1975 | Lange et al. |
| 4,046,514 A | 9/1977 | Johnston et al. |
| 4,633,886 A | 1/1987 | Bucaro, Jr. |
| 4,862,899 A | 9/1989 | Bucaro |
| 5,063,930 A * | 11/1991 | Nucci ........................ 600/366 |
| 5,140,986 A | 8/1992 | Klingner |
| 5,217,444 A | 6/1993 | Schoenfeld |
| 5,353,803 A | 10/1994 | Cerra |
| 5,425,377 A | 6/1995 | Caillouette |
| 5,577,512 A | 11/1996 | Caillouette |
| 5,660,790 A | 8/1997 | Lawrence et al. |
| 5,735,801 A | 4/1998 | Caillouette |

(Continued)

FOREIGN PATENT DOCUMENTS

| | | |
|---|---|---|
| CA | 2192004 C | 5/2006 |
| DE | 102009053341 B3 * | 7/2011 |
| WO | WO 9404916 A1 * | 3/1994 |

*Primary Examiner* — Adam J Eiseman
*Assistant Examiner* — Patrick Fernandes
(74) *Attorney, Agent, or Firm* — The Webb Law Firm

(57) ABSTRACT

A device and method for the collection and testing of mammalian fluid samples. The device consists of an outer sleeve and an inner swab whereby the inner swab fits into the internal cavity of the outer sleeve and is moveable within the outer sleeve. The outer sleeve contains testing means, such as a pH test or an amine release test within its internal cavity. A fluid sample is introduced to the device by way of a sample collection opening in the outer sleeve, which is received by the inner swab within the outer sleeve. The inner sleeve containing the sample is then moved through the outer sleeve so that it comes into contact with the testing means.

9 Claims, 3 Drawing Sheets

(56) References Cited

U.S. PATENT DOCUMENTS

| | | |
|---|---|---|
| 5,738,634 A | 4/1998 | Caillouette |
| 5,762,614 A | 6/1998 | Caillouette |
| 5,782,801 A | 7/1998 | Caillouette |
| 5,827,200 A | 10/1998 | Caillouette |
| 5,910,447 A | 6/1999 | Lawrence et al. |
| 5,916,176 A | 6/1999 | Caillouette |
| 5,928,165 A | 7/1999 | Caillouette |
| 5,998,161 A | 12/1999 | Caillouette |
| 6,013,036 A | 1/2000 | Caillouette |
| 6,019,734 A * | 2/2000 | Parkinson ............... 600/572 |
| 6,083,178 A | 7/2000 | Caillouette |
| 6,099,801 A | 8/2000 | Lawrence et al. |
| 6,117,090 A | 9/2000 | Caillouette |
| 6,190,331 B1 | 2/2001 | Caillouette |
| 6,283,927 B1 | 9/2001 | Caillouette |
| 6,390,991 B1 | 5/2002 | Caillouette |
| 6,402,705 B1 | 6/2002 | Caillouette |
| 6,406,441 B1 | 6/2002 | Caillouette |
| 6,409,680 B1 * | 6/2002 | Caillouette ............... 600/584 |
| 6,409,681 B1 | 6/2002 | Caillouette |
| 6,496,441 B2 | 12/2002 | Kono et al. |
| 6,544,196 B2 | 4/2003 | Caillouette |
| 6,627,394 B2 | 9/2003 | Kritzman et al. |
| 6,921,647 B2 | 7/2005 | Kritzman et al. |
| 7,314,752 B2 | 1/2008 | Kritzman et al. |
| 7,955,572 B2 * | 6/2011 | Hannant et al. ............... 422/406 |
| 2002/0058886 A1 | 5/2002 | Caillouette |
| 2003/0023189 A1* | 1/2003 | Kuo ............... 600/584 |
| 2005/0112547 A1* | 5/2005 | Youngkin ............... C12Q 1/04 435/4 |
| 2007/0073190 A1 | 3/2007 | Caillouette |
| 2007/0073192 A1 | 3/2007 | Caillouette |
| 2007/0141655 A1 | 6/2007 | Yee et al. |
| 2008/0009769 A1 | 1/2008 | Caillouette |

\* cited by examiner

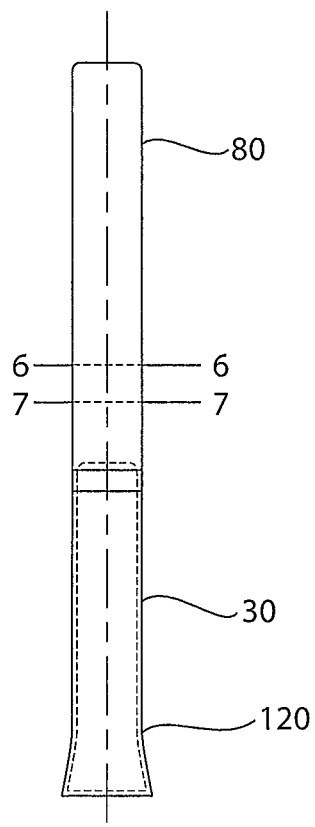 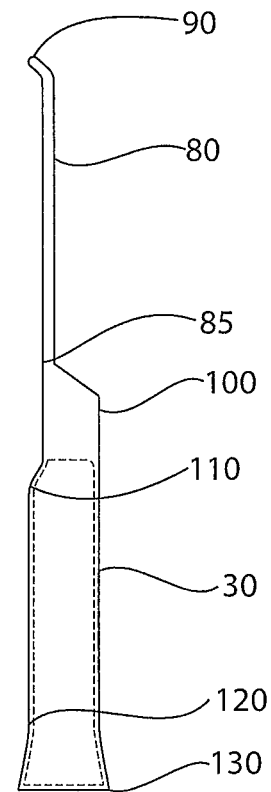
FIG. 9  FIG. 12
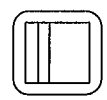 
FIG. 10  FIG. 11

FLUID SAMPLE COLLECTION AND TESTING DEVICE

FIELD OF THE INVENTION

The present invention relates to a sample collection and testing device and more specifically a device for the collection of a fluid sample from any externally accessible mammalian orifice. For example, a device for the collection, visual evaluation and testing of vaginal fluid samples for diagnosing bacterial and fungal infections.

BACKGROUND OF THE INVENTION

The vagina normally contains a number of microorganisms. Vaginal infections may occur as a result of the presence of certain quantities and/or types of bacteria, fungus (yeast) or parasite. Parasites such as trichomonas vaginalis are transmitted sexually whereas bacterial and yeast infections may occur even without sexual activity. Effective treatment depends on accurately determining the type of vaginal infection.

Bacterial vaginosis ("BV") is a disease of the vagina that occurs when the normal bacterial flora are disturbed. BV can be diagnosed by the presence of at least three of the following criteria, known as the Asmel criteria:
1. homogeneous discharge (colour and amount may vary);
2. the presence of clue cells (greater than 20%) under a microscope;
3. a vaginal pH of greater than 4.5; and
4. the release of a fishy odor on adding potassium hydroxide ("KOH") solution.

In trichomonas vaginalis (a parasitic infection) the vaginal fluid has the appearance of frothy, yellow-green vaginal discharge with a strong odor before the KOH test.

In a fungal, such as yeast infection, the vaginal fluid has the typical appearance of a whitish, thick appearance and texture, like cottage cheese and is odourless before and after the KOH test.

Vaginal infections are common and many women seek treatment of vaginal infections with over the counter remedies. Due to the common nature of these infections and the fact that many women seek their own remedies, there is a need for infected women, doctors and nurses to be able to collect a vaginal fluid sample and to easily identify potential bacterial or fungal infections. There is a need for a testing device which would allow the consumer or professionals to collect, examine, and then apply the sample to tests for pH, bacterially derived amines ("BDA") released with KOH solution, and other tests to diagnose potential infections. Such a testing device would be helpful in directing a woman to seek help from a physician and/or treat appropriately. One or more diagnostic tests, contained in a simple, easy-to-use, self-contained device could help to successfully treat BV and yeast infections and reduce the risk of subsequent associated problems (such as, pre-term labour, pelvic inflammatory disease ("PID"), increased risk of contracting sexually transmitted diseases such as HIV, etc.).

There are a number of ways in which fluid samples can be collected from the body and tested, including the use of a swab to collect a fluid sample and then application of the sample on the swab to a further device or location in order to test the sample for infectious agents or other indicia which aid in diagnosis of a disease or abnormality. More specifically and by way of example, there are numerous devices for collecting and testing vaginal fluid.

There is, currently, no all in one test available over the counter that permits collection of a sample of vaginal fluid, visual examination of its appearance for colour, consistency, and viscosity, and application of the sample to tests which would help distinguish pH, the presence of BDA's, and other tests to enable an accurate and/or differential diagnosis of fungal and bacterial infections. Proper diagnosis of vaginal infections reduces inappropriate treatments and the subsequent infections that arise from poor and/or improper treatment.

U.S. Pat. No. 5,738,634 discloses a stick device with a pH detector at one end for detecting the pH of vaginal moisture and a color measurement means. U.S. Pat. No. 5,425,377 includes a pH colorimetric measurement strip on the stick with the pH detector means.

U.S. Pat. No. 6,083,178 likewise discloses a stick device with a pH detector at one end (sized for application to a zone adjacent the wall of the vagina) for detecting the pH of vaginal moisture and additionally may include a protective layer over the pH detector whereby the vaginal moisture will penetrate the layer, but the pH detector will not come in contact with vaginal tissue. U.S. Pat. No. 6,283,927 also has a probe with pH detection means, whereby the probe is flat on at least one side. U.S. Pat. No. 6,496,441 additionally requires an edge presented generally longitudinally for limiting probe insertion into the vagina. All of these devices only detect pH and are thus not sufficient to make an accurate diagnosis of bacterial or fungal infection.

U.S. Pat. No. 5,998,161 discloses a method of detecting pathogenic bacteria wherein a moisture receiver is combined with a reactant(s) to produce a colour change upon contact with an amine, and a change in colour indicates the presence of pathogenic bacteria.

U.S. Pat. No. 6,013,036 includes a carrier with detecting means for detecting two conditions, the second of which is indicated as being for detection of pathogenic bacteria, by a "flowable fluid reactant container configured to allow controlled release of reactant fluid to react with bacteria containing vaginal or urethral moisture".

U.S. Patent Application Publication No. 2007/0073192 describes an apparatus and method, whereby a probe is inserted in the vagina and is manipulable to transfer vaginal moisture to a pH test and to a hydroxide carrier such that amines are detected.

None of the devices or methods set out in the prior art and devices currently available collect a body fluid sample and test it all within the device itself. Accordingly, there is a need for such an all in one sample collection and testing device and method of use.

SUMMARY OF THE INVENTION

The present invention is directed to a fluid sample collection and testing device comprising an outer sleeve having a closed first end, an open second end, an internal chamber, and a sample collection opening, an inner swab having a first end for receiving a fluid sample and a second end, said inner swab positioned within the internal chamber of the outer sleeve and movable through the second end of the outer sleeve, and at least one testing means positioned within the internal chamber. The at least one testing means of the fluid sample collection and testing device may be an amine release test and/or a pH indicator means. In an embodiment of the present invention a vent is positioned through the outer sleeve in proximity to the amine release test. In an embodiment of the present invention, the pH indicator means is capable of detecting a pH of 4.5 or greater and the pH of the pH indicator means is readable through a transparency in the outer sleeve.

The present invention is also directed to a fluid sample collection and testing device comprising an outer sleeve having a sample collection opening, an internal chamber and one or more internal testing means, an inner swab having a fluid receptor platform that aligns with the sample collection opening, said inner swab moveable through the internal chamber of the outer sleeve such that a fluid sample contacts the one or more testing means. The at least one testing means of the fluid sample collection and testing device is an amine release test and/or a pH indicator means. In an embodiment of the present invention a vent is positioned through the outer sleeve in proximity to the amine release test. In an embodiment of the present invention, the pH indicator means is capable of detecting a pH of 4.5 or greater and the pH of the pH indicator means is readable through a transparency in the outer sleeve.

The present invention is directed to a method for testing a fluid sample comprising the steps of applying the fluid sample to the first end of the inner swab through the sample collection opening of the device of the present invention and moving the inner swab out of the outer sleeve whereby the fluid sample contacts the at least one testing means.

The present invention is directed to a method for testing a vaginal fluid sample comprising the steps of applying the vaginal fluid sample to the first end of the inner swab through the sample collection opening of the device of the present invention, observing the sample, moving the inner swab out of the outer sleeve whereby the fluid sample contacts the pH indicator means and the amine release test, sniffing for an odour from the vent and viewing the pH of the indicator means.

The present invention is also directed to a method for testing mammalian fluid samples comprising the steps of introducing a sample to a sample collection and testing device by way of a sample collection opening of an outer sleeve having an internal chamber which has testing means, and an inner swab with a fluid receptor platform movable in the internal chamber, and moving the inner swab in the inner chamber so that the sample contacts the testing means.

These and other features and advantages of the present invention will be apparent to those skilled in the art from the following description of the example embodiments and the drawings.

BRIEF DESCRIPTION OF THE DRAWINGS

FIG. 9 is a front view of the inner swab.

FIG. 10 is a cross-sectional view of the inner swab taken along line 6-6 of FIG. 9.

FIG. 11 is a cross-sectional view of the inner swab taken along line 7-7 of FIG. 9.

FIG. 12 is a side view of the inner swab.

DETAILED DESCRIPTION OF THE INVENTION

In an example embodiment of the present invention, the sample collection and testing device is comprised of an inner swab and an outer sleeve. This device may be used for the collection of a fluid sample from any externally accessible mammalian orifice (such as, oral, rectal, vaginal, wound or incision). The figures illustrate an example embodiment of the present invention, namely a device for the collection, visual evaluation and testing of fluid samples for diagnosing bacterial and fungal infections, but, the description below refers to the use of the device with vaginal fluid. However, as will be further described the device of the present invention is generally adaptable for collection and testing of mammalian body fluid samples.

Figure 1:
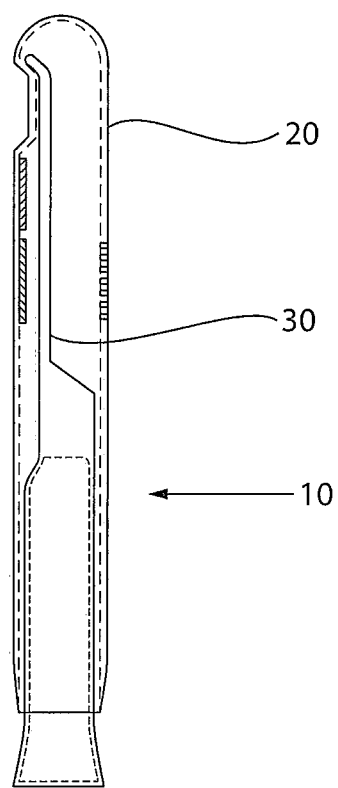
FIG. 1 is a side view of the inner swab within the outer sleeve of an embodiment of the present invention in a sample receiving position.
Figure 2:
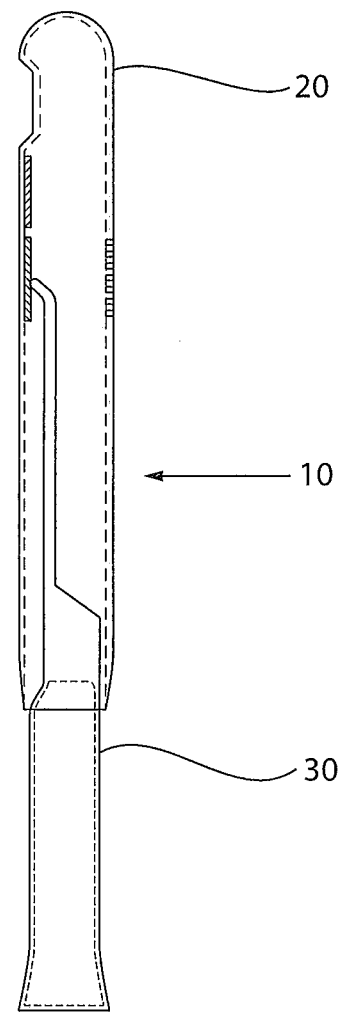
FIG. 2 is a side view of the inner swab within the outer sleeve of an embodiment of the present invention in a testing position.

Referring to the figures, FIG. 1 shows an example embodiment of a sample collection and testing device for vaginal fluid. This device 10 is shown in a sample receiving position in FIG. 1 and comprises an outer sleeve 20 and inner swab 30. FIG. 2 also shows the device 10 with outer sleeve 20 and inner swab 30, this time in a testing position.

Figure 3:
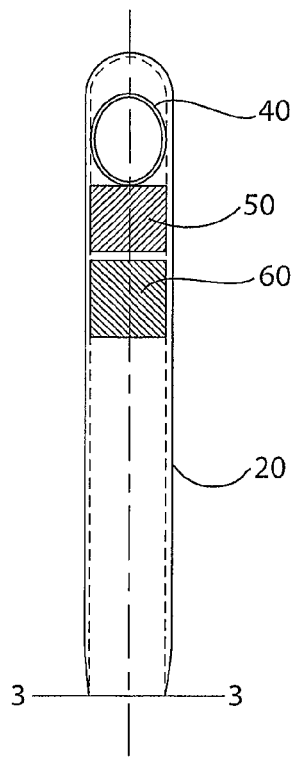
FIG. 3 is a front view of the outer sleeve with a transparent top surface.
Figure 4:
FIG. 4 is a cross-sectional view of the outer sleeve taken along line 3-3 of FIG. 3.
Figure 5:
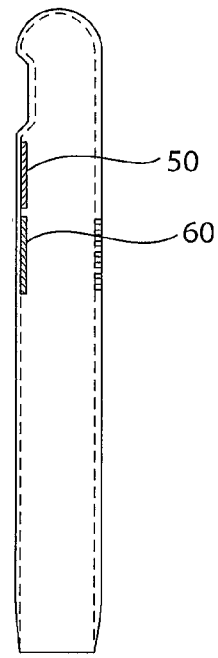
FIG. 5 is a side view of the outer sleeve.
Figure 7:
FIG. 7 is a cross-sectional view of the outer sleeve taken along line 4-4 of FIG. 6.

The outer sleeve 20 is further illustrated in FIG. 3 which shows the fluid collection opening 40 as an opening in the front face of the outer sleeve 20. The outer sleeve has a closed first end, an open second end and an internal chamber. The open second end of the outer sleeve is tapered. A benefit of the tapered outer sleeve is that it permits the delineation by touch of where the outer sleeve ends and the inner swab withdrawal mechanism begins.

The front face in FIG. 3 is transparent to reveal two test sites inside, namely, a pH indicator means 50 and a potassium hydroxide ("KOH") patch 60. As will be understood, any other tests, either presently existing or developed in future, for pH or that allow the release of amines and work with a fluid sample could be used in the present invention. The device of the present invention may be used with any tests which provide helpful information on the nature of a fluid sample. Although an example embodiment is discussed here, an alternative to the KOH patch is to use any test that allows the release of amines from a fluid sample, which test will also be referred to herein as an amine release test.

Figure 6:
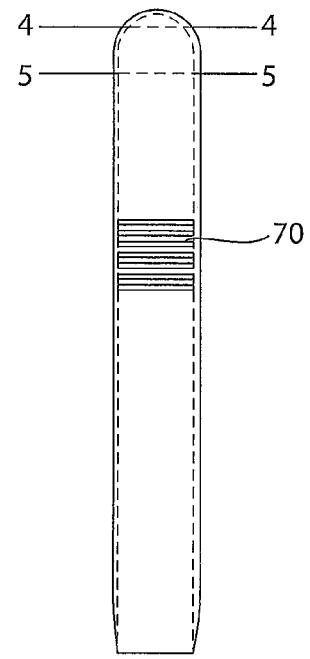
FIG. 6 is a back view of the outer sleeve.
Figure 8:
FIG. 8 is a cross-sectional view of the outer sleeve taken along line 5-5 of FIG. 6.

FIG. 6 shows a back view of the outer sleeve 20 with a vent 70 located in proximity to the KOH patch 60. As shown in FIGS. 1 and 2, most of the inner swab 30 is positioned in the internal chamber of the outer sleeve and is moveable through the open second end of the outer sleeve.

FIG. 9 shows the front view of an inner swab 30. FIG. 12 shows the side view of the inner swab 30 with a fluid receptor platform 80 proximal to the first end 90. Below juncture 85, the inner swab 30 widens to middle portion 100 with a further widening 110 all of which may be received by the internal chamber of the outer sleeve. The inner swab begins to flare out 120 close to the second end 130 of the inner swab. The portion of the inner swab from around the flare out 120 to the second end 130 may not be received by the internal chamber of the outer sleeve. This portion of the inner swab extends beyond the open second end of the outer sleeve in both the sample receiving position and the testing position of the device.

In an example embodiment of the present invention, the tapered open second end of the outer sleeve and portion of the inner swab from the flare out 120 to the second end 130 are adapted to easily pull the inner swab 30 out of outer sleeve 20 and also so the sample received by the device does not leak out of the device in both the sample receiving position and testing position.

It is understood that the device of the present invention could include only a pH indicator (with no amine release test), or only an amine release test (and no pH indicator) or another test or combination of tests. It is further understood that the device of the present invention could include any indicator or patch in it that would permit testing of a body fluid within the device. It is further understood that while the outer sleeve of the example embodiment is transparent, the device could have a transparent, opaque or semi-transparent outer sleeve or a transparent, opaque or semi-transparent inner swab depending on the nature of the test or tests, e.g. opaque for only sniff test.

The present invention is directed to a method of collecting and testing body fluid. In an example embodiment of the present invention, the closed first end of a vaginal fluid collection and testing device 10 as described above and as shown in FIG. 1 in a sample receiving position is inserted into the vagina, pressed against the vaginal wall whereby fluid will collect in the fluid collection opening 40 and then the device 10 is withdrawn. (Alternatively, a probe can be inserted into the vagina and the vaginal fluid collected on the probe can be deposited in the opening 40.) The vaginal fluid can then be sniffed and examined in the opening 40 which appearance is another criterion in determining the type of infection (and vaginal fluid appearance will be described below). Referring to FIGS. 1 and 2, the inner swab 30 is pulled by its second end 130 outwardly from the outer sleeve 20 up to about further widening 110 of the inner swab thus causing the fluid sample (not shown) in the opening 40 to be dragged over the pH indicator means 50 and the KOH patch 60. The entire device can be discarded in one piece on completion of the test.

A pH colourimetric measurement chart (not shown) may be used to evaluate the pH of the vaginal fluid by comparison of the chart with the colour of the pH indicator means 50 as seen through the transparent top face of the outer sleeve 20. The KOH patch 60 contains an effective amount of KOH, for example a 10% concentration absorbed onto the test surface, such that if there is trichomonal vaginitis or bacterial vaginosis in the vaginal fluid the amines are released by contact with the KOH to cause malodor, typically characterized as a fishy smell. The bacterially-derived amines released by the sample are detected by smell when released through the vent 70. This so called 'whiff test' indicates the presence of bacterially-derived amines.

The pH indicator means may include a means for detection of pH of 4.5 or greater and another means for detection of pH of between 3.0 and 6.0. The transparent outer sleeve allows for the visual assessment of the pH and the quality of the specimen. The odour from the whiff test can be detected by a vent 70 placed on the top face or anywhere on the outer housing 20 such that it is in proximity to the KOH patch 60.

The above example embodiment of the present invention may be adapted to include only one of the pH indicator means 50 or KOH patch 60 or to add further tests. The opening 40 can also be located such that the inner swab is pushed in and over the test locations rather than being pulled out, or can be pulled in spiral fashion across the test means and patches.

In an example embodiment of the present invention, the outer sleeve 20 is transparent allowing for the sample collected in the inner swab 30 to be seen at all times. Accordingly, the described vaginal fluid collection and testing device allows for the visual examination of the vaginal sample in the opening both prior to an after application to the tests contained within the device.

A yeast/fungal infection would not trigger an odour reaction; as well, the pH indicator would show <4.5. A trichomonal infection would result in the same outcome as bacterial vaginosis testing (pH and odour reaction); the treatment for bacterial vaginosis (caused by gardnerella vaginalis) and trichomonas is identical.

Any reagent strip(s) or tests can be positioned in place of the pH and KOH (or amine release test). This would depend on the context of the diagnostic test, but other tests commonly performed on fluids such as urine include specific gravity, glucose, ketones, protein, blood (hemoglobin), leukocytes, urobilinogen, and bilirubin. The device of the present invention is designed to isolate the testing strips within the device so at to prevent them from getting into direct contact with any body surface area, thus avoiding the potential for any harm through chemical irritation/contamination or misdiagnosis from contact with other than the desired fluid sample.

This all in one device and method for collection and testing for bacterial vaginosis, is adapted to also test for other maladies in which a fluid sample can be collected. In addition to personal use and use administered by a health professional, such a device could be used in a laboratory setting wherein the fluid sample could be collected off site and placed in the device for testing in the lab.

Types of fluids for which this device could be used include but are not limited to urine, mucous, serum, sputum, vaginal fluid, seminal fluid, blood and purulent discharge. This device may also be used with anything that can be modified and/or reduced to fluid form that may be applied to the device for testing. Since certain testing means do not work with pigmented samples, for example blood, the fluid may need to be treated or the testing means modified to adapt to the presence of pigment.

From the above detailed description of the invention, the operation and construction of same should be apparent. While there are herein shown and described example embodiments of the invention, it is nevertheless understood that various changes may be made with respect thereto without departing from the principle and scope of the invention as measured by the following claims.

What is claimed is:

1. A fluid sample collection and testing device for the collection of a fluid sample from an externally accessible mammalian orifice, the device comprising:

an outer sleeve having a sample collection opening, an internal chamber and at least one internal testing means positioned within the internal chamber, the outer sleeve having a closed first end and an open second end;

an inner swab having a first end provided with an angled fluid receptor platform, the inner swab being movable through the second end of the outer sleeve between a sample receiving position, in which the fluid receptor platform aligns with the sample collection opening for receiving a fluid sample through the sample collection opening, and a sample testing position, in which the angled fluid receptor platform contacts the at least one internal testing means, wherein when the inner swab moves through the second end of the outer sleeve the angled fluid receptor platform is dragged over the at least one internal testing means, wherein the fluid receptor platform is isolated within the outer sleeve in both the sample receiving and the sample testing positions and wherein the inner swab engages the open second end of the outer sleeve in the sample receiving position and the sample testing position which prevents the sample from leaking from the device.

2. The device of claim 1, in which the at least one testing means is an amine release test.

3. The device of claim 1, in which the at least one testing means is a pH indicator means.

4. The device of claim 1, in which the at least one testing means is an amine release test, and the device additionally comprises a vent positioned through the outer sleeve in proximity to the amine release test.

5. The device of claim 1, in which the at least one testing means comprises a pH indicator means and an amine release test, and the device additionally comprises a vent positioned through the outer sleeve in proximity to the amine release test.

6. The device of claim 4, wherein the pH indicator means is capable of detecting a pH of 4.5 or greater and the pH of the pH indicator means is readable through a transparency in the outer sleeve.

7. The device of claim 5, wherein the pH indicator means is capable of detecting a pH of 4.5 or greater and the pH of the pH indicator means is readable through a transparency in the outer sleeve.

8. The device according to claim 1, wherein the sample collection opening is an opening in a front face of the outer sleeve, adjacent the closed first end of the outer sleeve.

9. The device according to claim 1, wherein the second end of the inner swab extends beyond the second end of the outer sleeve.

* * * * *